United States Patent
Selvaraj

(10) Patent No.: US 11,647,967 B2
(45) Date of Patent: May 16, 2023

(54) GENERATING AUTOMATED ALARMS FOR CLINICAL MONITORING

(71) Applicant: Vital Connect, Inc., Campbell, CA (US)

(72) Inventor: Nandakumar Selvaraj, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 432 days.

(21) Appl. No.: 15/272,879

(22) Filed: Sep. 22, 2016

(65) Prior Publication Data

US 2018/0078219 A1    Mar. 22, 2018

(51) Int. Cl.
*A61B 5/00*    (2006.01)
*A61B 5/024*    (2006.01)
*A61B 5/145*    (2006.01)
*A61B 5/08*    (2006.01)

(52) U.S. Cl.
CPC ............ *A61B 5/746* (2013.01); *A61B 5/7203* (2013.01); *A61B 5/7221* (2013.01); *A61B 5/024* (2013.01); *A61B 5/0816* (2013.01); *A61B 5/14542* (2013.01); *A61B 5/6833* (2013.01); *A61B 5/7207* (2013.01)

(58) Field of Classification Search
CPC ...................................................... A61B 5/746
See application file for complete search history.

(56) References Cited

U.S. PATENT DOCUMENTS

| | | | |
|---|---|---|---|
| 5,919,141 A * | 7/1999 | Money | A61B 5/02055 600/483 |
| 6,102,856 A * | 8/2000 | Groff | A61B 5/02055 128/903 |
| 6,198,394 B1 * | 3/2001 | Jacobsen | A61B 5/1112 340/573.1 |
| 7,529,790 B1 * | 5/2009 | Sayal | G06F 17/18 708/422 |
| 2007/0173761 A1 * | 7/2007 | Kanderian, Jr. | A61B 5/14532 604/131 |
| 2012/0095304 A1 * | 4/2012 | Biondi | A61B 5/0402 600/301 |
| 2012/0245439 A1 * | 9/2012 | Andre | A61B 5/0205 600/310 |
| 2016/0242672 A1 * | 8/2016 | Mikoshiba | A61B 5/6843 |

* cited by examiner

*Primary Examiner* — Hyun D Park
(74) *Attorney, Agent, or Firm* — Shih IP Law Group, PLLC

(57) ABSTRACT

A method and system for providing health-monitoring alarm management have been disclosed. In a first aspect, the method comprises detecting at least one vital sign signal using a wearable sensor device and managing an alarm mechanism of the wearable sensor device based on the at least one vital sign signal. In a second aspect, the system comprises a sensor for detecting at least one vital sign signal, a processor coupled to the sensor, and a memory device coupled to the processor, wherein the memory device stores an application which, when executed by the processor, causes the processor to manage an alarm mechanism of the wearable sensor device based on the at least one vital sign signal.

20 Claims, 9 Drawing Sheets

GENERATING AUTOMATED ALARMS FOR CLINICAL MONITORING

FIELD OF THE INVENTION

The present invention relates to wearable sensor devices, and more particularly, to wearable sensor devices that are utilized to generate automated alarms for clinical monitoring.

BACKGROUND

Wearable sensor devices are utilized to continuously monitor health related parameters (e.g., vital signs) of a user in clinical monitoring situations. Alarms are commonly embedded within these wearable sensor devices or are part of other external systems coupled to the wearable sensor devices. These alarms are necessary to alert the clinicians about any abnormal deviations in the user's vital signs from desired normal values and to indicate the possibility of required clinical interventions. These alarms play a major role in preventing deterioration of patients unattended in hospitals/home, improve patient safety, and help save lives.

Conventional alarm systems suffer from nuisance alarms (i.e., false positive alarms sounded even though there is no potential issue) due to artifacts, movements and disconnection. These nuisance alarms are extremely frequent causing distrust and insensitivity to alarms, prevent timely clinical interventions, and delay patient care in adverse conditions. Therefore, there is a strong need for a cost-effective and efficient solution that overcomes the aforementioned issues. The present invention addresses such a need.

SUMMARY OF THE INVENTION

A method and system for providing health-monitoring alarm management have been disclosed. In a first aspect, the method comprises detecting at least one vital sign signal using a wearable sensor device and managing an alarm mechanism of the wearable sensor device based on the at least one vital sign signal.

In a second aspect, the system comprises a sensor for detecting at least one vital sign signal, a processor coupled to the sensor, and a memory device coupled to the processor, wherein the memory device stores an application which, when executed by the processor, causes the processor to manage an alarm mechanism of the wearable sensor device based on the at least one vital sign signal.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
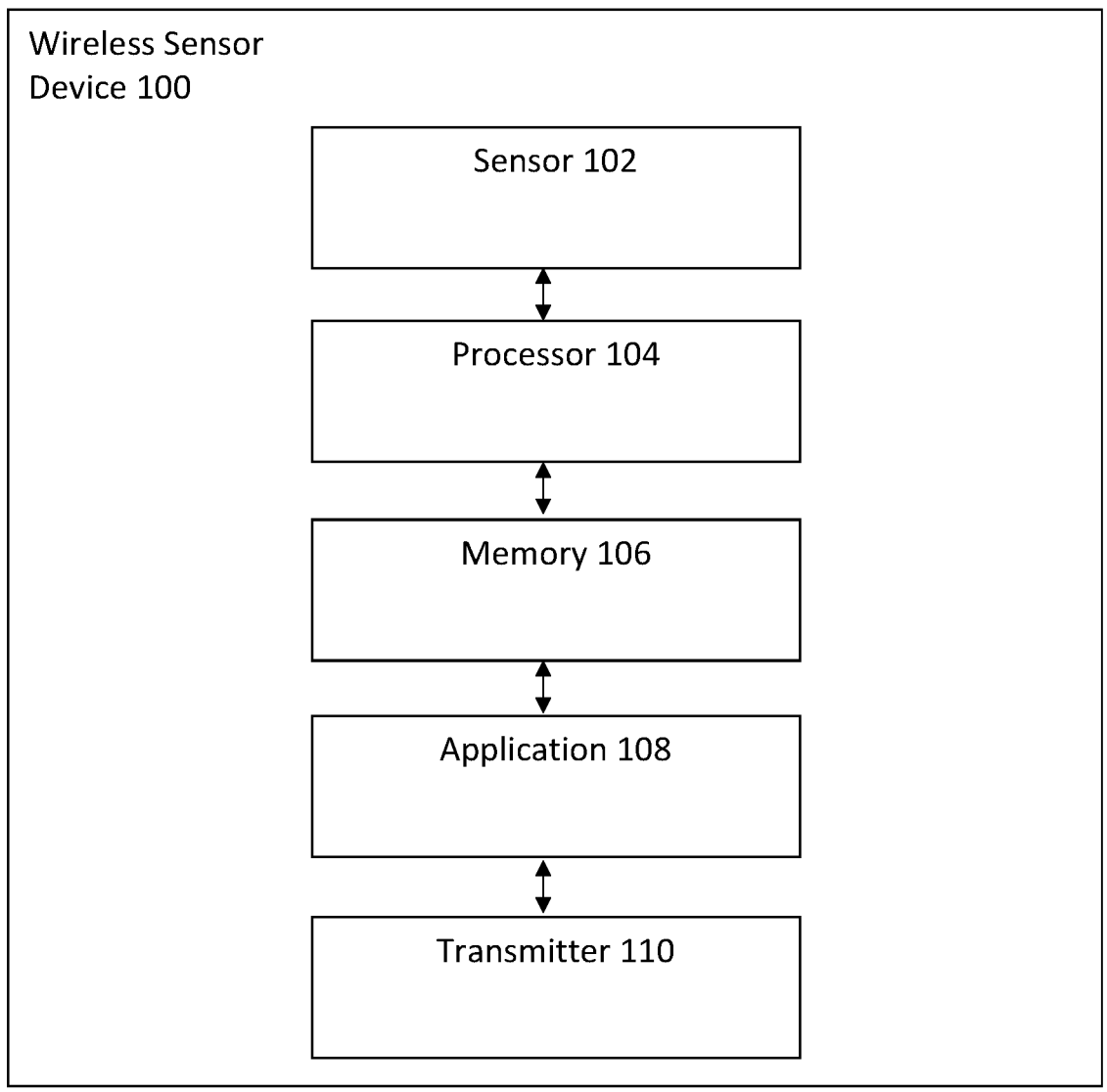
FIG. 1 illustrates a wireless sensor device in accordance with an embodiment.

The present invention relates to wearable sensor devices, and more particularly, to wearable sensor devices that are utilized to generate automated alarms for clinical monitoring. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Wireless wearable sensor devices (wearable sensor devices including patch sensors) are utilized to continuously and/or remotely monitor the health of a user. Wearable sensor devices either have embedded alarm systems or are coupled to external alarm systems to help notify clinicians of abnormal vital signs during clinical monitoring settings.

Conventional alarm systems suffer from numerous issues pertaining to false alarms (i.e., nuisance alarms that sound when the user's vital signs are still within normal ranges or not indicative of any major abnormalities that require immediate clinician intervention). In addition, the customization of vital sign limits in patients for one or more levels of alarms requires dedicated professionals (possibly on a one on one basis) to learn the patterns in each user's vital signs over a predetermined (prolonged) duration. This would enable necessary adjustments to be made in the vital sign limits as the patterns are learned to mitigate nuisance alarms.

The usage of dedicated professionals is very costly, time-consuming and impractical in hospital and telemetry situations. The requirement of this approach results in low compliance in medical progressive care unit nurses regarding the tailoring of parameters to the individuals particularly after carrying out clinical interventions in other units. A method and system in accordance with the present invention provides a smart alarm management system that greatly improves compliance and enables effective prompt patient clinical intervention. The smart alarm management system preserves true positive alarms related to a user's deteriorating condition and greatly reduces the false positive alarms. In a first embodiment, the present invention filters artifacts/spikes in the vital sign responses using a statistical filtering methodology. In a second embodiment, the present invention automatically generates alarms using magnitudes and durations of the vital sign responses. In a third embodiment, the present invention automatically adapts the vital sign alarm limits to provide dynamically customized alarm limits for each patient.

To describe the features of the present invention in more detail, refer now to the following description in conjunction with the accompanying Figures.

FIG. 1 illustrates a wireless sensor device 100 in accordance with an embodiment. In one embodiment, the wireless sensor device 100 is a wearable sensor device that utilizes a flexible circuit design in a patch form factor (i.e., the wearable device is a patch that adheres to the user to measure the user's vital body signs) that is either entirely disposable (both the adhesive patch portion and the electronic module and sensor device portion) or partially disposable (e.g., the electronic module and sensor device portion being reusable and the adhesive patch portion being disposable).

In one embodiment, the wireless sensor device 100 ("wearable sensor device" or "wearable device") includes at least one sensor 102, at least one processor 104 coupled to the at least one sensor 102, at least one memory 106 coupled to the at least one processor 104, at least one application 108 coupled to the at least one memory 106, and at least one transmitter 110 coupled to the at least one application 108. One of ordinary skill in the art readily recognizes that the wireless sensor device 100 can include other components not aforementioned and that the components of the wireless sensor device 100 can be coupled in a variety of different ways from the orientation shown in FIG. 1 and that would be within the spirit and scope of the present invention.

In one embodiment, the wireless sensor device 100 is attached to a user via an adhesive patch to detect various physiological signals including the user's vital signs via the at least one sensor 102. The at least one sensor 102 obtains the physiological signal data from the user, which is transmitted to the at least one memory 106 and in turn to the at least one application 108 via the at least one processor 104. The at least one processor 104 executes the at least one application 108 to process, transform, and analyze the data to obtain critical health-related information of the user including but not limited to the user's vital signs.

In one embodiment, the at least one application 108 utilizes embedded algorithms and processes to process, transform, and analyze the data. By executing the at least one application 108 to process the data detected by the at least one sensor 102, the overall functioning of the wireless sensor device 100 is improved and the technical field related to determining the user's temperature is also improved. In addition, the data processing analysis can lead to the generation of alarms based upon whether the vital signs are within normal boundaries or abnormal.

The information (including the potential generated alarms) is transmitted to the at least one transmitter 110 and in turn relayed to another user (such as a clinician or nurse) or device for further processing, analysis, and storage. In another embodiment, the at least one transmitter 110 transmits the various physiological signals detected in raw form by the at least one sensor 102 to a remote device/server (e.g., smartphone, cloud-based server, etc.) for further processing, analysis, and storage.

In one embodiment, the at least one sensor 102 is any of a microelectromechanical systems (MEMS) multi-axial (e.g., tri-axial) accelerometer, an embedded sensor with electrodes, a temperature sensor, and a photoplethysmography sensor. In one embodiment, the at least one processor 104 is a microprocessor. One of ordinary skill in the art readily recognizes that a variety of device types and designs can be utilized for the at least one sensor 102, the at least one processor 104, the at least one memory 106, the at least one application 108, and the at least one transmitter 110 and that would be within the spirit and scope of the present invention.

In addition, one of ordinary skill in the art readily recognizes that a variety of wireless sensor devices can be utilized including but not limited to wearable sensor devices, a wireless sensor device in a patch form-factor, the Vital Connect HealthPatch® and/or VitalPatch® wearable devices, electrocardiograph devices, smart watches, photoplethysmographs, pulse oximeters, uni-axial accelerometers, bi-axial accelerometers, tri-axial accelerometers, gyroscopes, and pressure sensors and that would be within the spirit and scope of the present invention.

In one embodiment, the HealthPatch® and VitalPatch® wearable devices are disposable adhesive patch biosensors (either partially or fully disposable) worn on the user's chest or another location of the body. The wearable devices incorporate at least two surface electrodes with a hydrogel-like material on the bottom, at least one battery, at least one electronic module with an embedded processor and other electronic components and circuitry (that is reusable in the HealthPatch® and that is fully disposable in the VitalPatch®), at least one MEMS tri-axial accelerometer, and at least one Bluetooth Low Energy (BLE) transceiver.

In one embodiment, the wearable device facilitates continuous and automated monitoring of a plurality of physiological signals. In this embodiment, after the wearable device detects the plurality of physiological signals (in raw form) via a plurality of internal and embedded sensors, the electronic module of the wearable device utilizes a plurality of algorithms (e.g., firmware algorithms) and processing techniques to process and transform the raw waveforms of the plurality of physiological signals into actionable data outputs which are then transmitted as a stream of processed physiological variables via the BLE transceiver/link as encrypted data to a relay such as a smartphone, where the live (real-time) streams of data can be viewed, stored, and further processed/analyzed.

The method and system in accordance with the present invention provides a smart alarm management system that carries out at least the following activities: effectively filtering out artifacts/spikes in vital signs using a statistical filtering method which improves upon conventional magnitude based alarms, controlling the frequency of alarms by features of the vital signs and automatically generating alarm signals based on the features (e.g., fixed magnitude threshold and duration) of the vital sign response, adaptively varying the alarm thresholds and automatically controlling the alarms based on the features (e.g., adaptive magnitude threshold and duration). The smart alarm management system drastically reduces the false positive alarms and preserves true positive alarms for true elevations (or variances or abnormalities) the vital sign responses of the user. Therefore, the smart alarm management system provides an effective alarm system that enables 24 hour monitoring in clinical and home settings.

In a first embodiment, a method and system in accordance with the present invention provide a method for artifact/spike removal using a statistical filtering methodology. Frequent false alarms are undesirable and a distraction in clinical monitoring settings. Artifacts and/or spikes in the vital sign response (i.e., physiological signals detected by the wearable sensor device) are inherent and false alarms are typically generated due to these artifacts/spikes in the detected signal. By utilizing statistical filtering, the artifacts and spikes are removed from the vital sign response/signal, and false positive alarms (i.e., alarms that go off indicating an issue with the user/patient's vital signs when in actuality there are no issues warranting alarm) are drastically reduced.

The artifacts/spikes are removed by identifying the spikes as outliers when the values of the vital sign response are outside a statistical boundary (e.g., $\mu \pm \alpha^* \sigma$, where $\mu$ is the mean, $\sigma$ is the standard deviation, and $\alpha$ is a coefficient or factor). After the identification of the spikes, the spikes are replaced with a moving average value (e.g., $\mu$). On the other hand, when the values of the vital sign response are within the statistical boundary, the values are not marked as spikes and are unchanged. As a result, the method only removes artifacts/spikes from the vital sign response signal. In one embodiment, the method is utilized for heart rate (HR) vital signs. In another embodiment, the method is utilized for other vital sign measurements including but not limited to breathing rate (BR) and blood oxygen saturation (SpO2).

Figure 2:
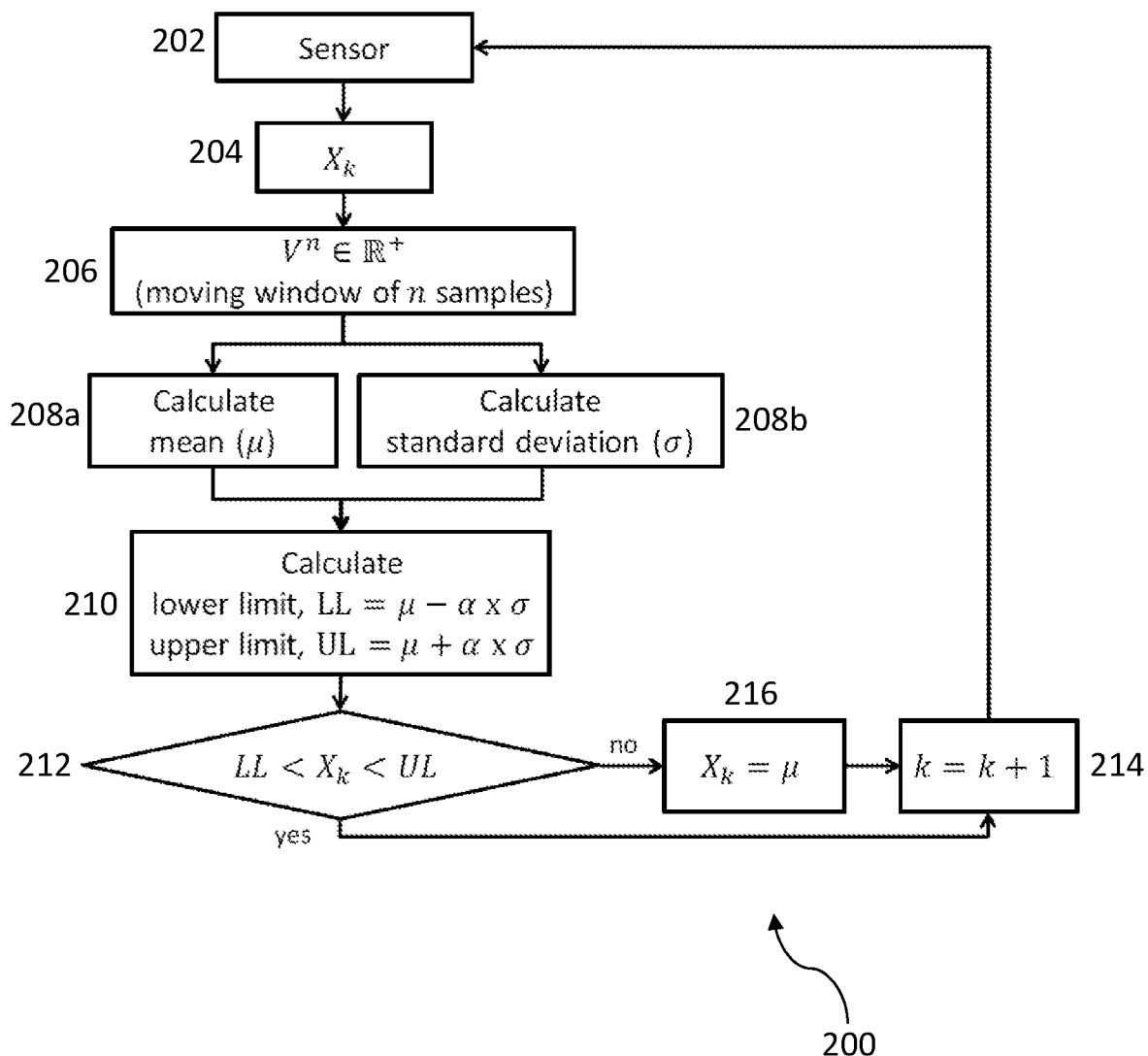
FIG. 2 illustrates a block diagram of a method for artifact removal using statistical filtering in accordance with an embodiment.

FIG. 2 illustrates a block diagram of a method 200 for artifact removal using statistical filtering in accordance with an embodiment. The method 200 starts with a wearable sensor device (such as the wearable sensor device 100) being attached to a user/patient for measuring/detecting a plurality of vital sign responses/signals, via step 202. The wearable sensor device continuously generates a vital sign variable X and consider a $K^{th}$ sample of X as $X_k$, via step 204, which is input to a moving window of n samples, via step 206, that shifts/slides forward by excluding the $1^{st}$ sample of the window and including the latest sample (e.g., K) in the window as $n^{th}$ sample. In one embodiment, the moving window of n samples is a real positive array denoted $V^n = \{X_{k-n+1}, X_{k-n+2}, \ldots, X_k\}$ where the number of samples n includes but is not limited to 10, 20, and 30 samples and X is a vital sign (e.g., HR). The method 200 calculates a mean ($\mu$), via step 208a, and a standard deviation ($\sigma$), via step 208b using the current n samples of the moving window $V^n$.

After calculating both the mean and standard deviation via steps 208a-b, the method 200 calculates a lower limit (LL) and an upper limit (UL) which represent the lower and upper statistical boundaries respectively, via step 210. The lower limit (LL) is calculated as $LL = \mu - \alpha^* \sigma$ and the upper limit (UL) is calculated as $UL = \mu + \alpha^* \sigma$ where alpha ($\alpha$) is a factor or coefficient including but not limited 1, 1.1, 1.2 ..., 2.0. Once the lower and upper limit boundaries (LL and UL) are determined, the current sample $X_k$ is compared to the lower and upper limits, via step 212.

If the current sample $X_k$ is determined to be within the boundaries (yes), the current sample value $X_k$ is not modified and the sample number k is incremented (i.e., k=k+1), via step 214, and the method 200 repeats the above process for the next or upcoming sample of $X_k$ provided by the wearable sensor device. If the current sample $X_k$ is not determined to be within the boundaries (no), the current sample $X_k$ is determined, by the wearable sensor device, to be an outlier or artifact value and is replaced with the previously determined mean ($\mu$) value, via step 216. Then the sample number k is incremented (i.e., k=k+1), via step 214, and the method 200 repeats the above process for the next or upcoming sample of $X_k$ provided by the wearable sensor device. Thus, the method 200 detects the outlier/artifact values present in the vital sign signal and filters out artifacts by replacing them with the moving average values.

Figure 3:
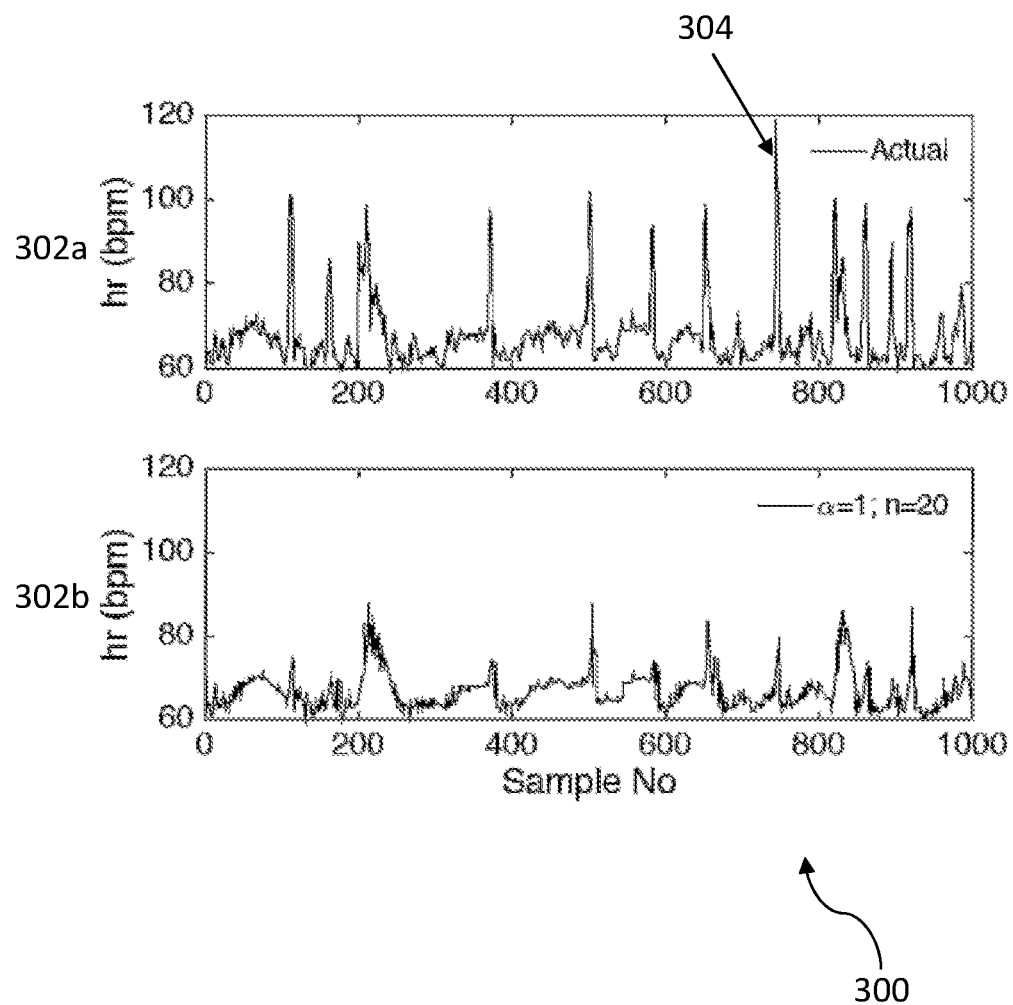
FIG. 3 illustrates a diagram of heart rate (HR) artifact removal using a wearable sensor device in accordance with an embodiment.

FIG. 3 illustrates a diagram 300 of heart rate (HR) artifact using a wearable sensor device in accordance with an embodiment. The top graph 302a of the diagram 300 depicts a heart rate (HR) signal consisting of a plurality of artifacts and/or spikes including artifact/spike 304. The bottom graph 302b of the diagram 300 depicts the filtered HR signal from the plurality of artifacts using the method 200. In the bottom graph 302b, the coefficient $\alpha$ is selected as 1.0 and the number of samples of the moving window n is selected as 20 among other values as described before.

In FIG. 3, both graphs have heart rate (HR) in beats per minute (bpm) across the y-axis and the sample number across the x-axis. Thus, the method 200 is effective in eliminating the large spikes as presented in the HR signal of the bottom graph 302b and also retaining a low frequency trend and the variance of the HR signal. The method 200 also varies the attenuation of high frequency oscillations present in the HR signal by increasing the number of samples of moving window n.

Alarms in health/clinical monitoring settings are typically generated based on a magnitude of the vital signs (e.g., HR, BR, SpO2, etc) alone and produce undesirable outcomes for patient care. In addition to removing artifacts/spikes from the vital sign signals, a method and system in accordance with the present invention also automatically manages a plurality of clinical and remote monitoring alarms. The method and system in accordance with the present invention automatically manages the onset and offset of alarms based on not only vital sign signal magnitudes but also the duration of the vital sign signal magnitudes above and/or below a predetermined and fixed/static threshold.

By automatically managing the alarms using signal magnitudes and durations with respect to set boundaries/thresholds, false positive alarms are reduced and true positive alarms are preserved thereby effectively controlling the frequency of the alarms associated with the monitoring of the user/patient via a wearable sensor device. In one embodiment, alarms with distinct magnitude thresholds can be identified as different levels and the levels can be differentiated in a variety of ways including but not limited to the tone/type of the alarm sounds (e.g., a whistle for one level and a bird chirping for another level), the color codes displayed on the wearable sensor device's display or a remote monitor's display, and the notifications with different alarm level numbers.

In one embodiment, a predetermined and embedded table within the application of the wearable sensor device to determine when to sound/onset the alarms. The table includes examples of different levels of alarms for vital sign magnitudes and durations of elevated levels (elevation)/decreased levels above/below the respective threshold. The elevation (e.g., threshold set at 100 bpm for HR and the user's HR is detected by the wearable sensor device as 110 bpm) is required to sustain for a minimal duration (e.g., 20 seconds) to affirm a true elevation thereby providing an onset of the associated alarm. The automated alarm management method and system reduces the false positive alarms that occur from artifacts/spikes without requiring any additional filtering of the artifacts/spikes as described by the method 200.

For example, the table could denote alarm levels 1, 2, 3, and 4 and HR magnitudes (in bpm) of greater than or equal to 100, 110, 129, and 139 associated with the alarm levels 1-4 respectively. In addition, each alarm level 1-4 is triggered when the HR elevation sustains above the respective threshold for a desired time duration (in seconds) including but not limited to 20, 40, and 60 seconds. Thus, the magnitude threshold determines which level of alarm, but sustained elevation above that magnitude threshold for the set elevation duration only sets off the respective alarm level. If the elevation does not sustain for that duration, the alarm will not be triggered. Therefore, the physiological signal magnitude must be greater than or equal to the magnitude threshold and must last for the set duration to set-off the alarm.

Therefore, an alarm (levels 1-4) will onset/sound if the user's HR (or other type of vital sign including but not limited to BR) is elevated above a certain threshold (e.g., if the threshold of the HR is set to 100 bpm, then anything above or equal to a HR of 100 bpm) and the detected elevation remains for a predetermined duration (any of 20, 40, or 60 seconds).

Figure 4:
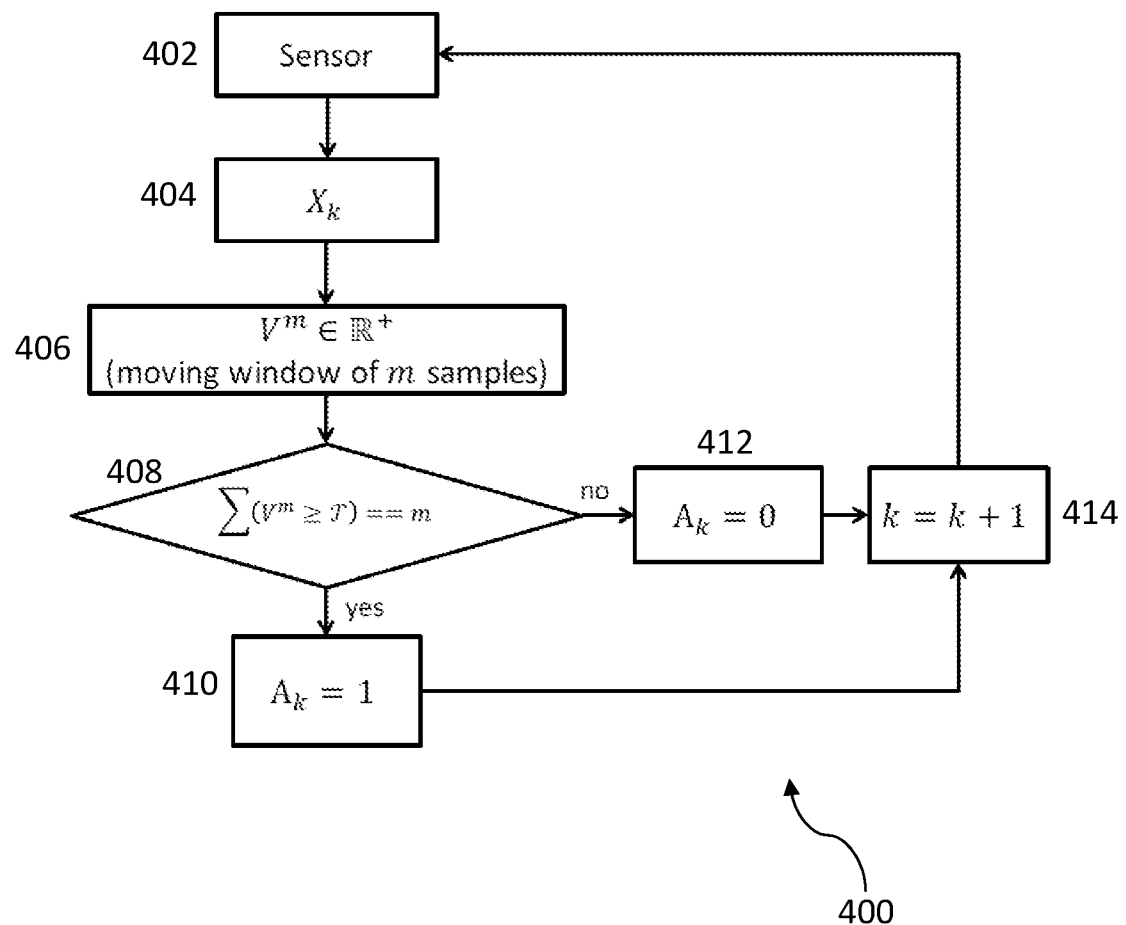
FIG. 4 illustrates a block diagram of a method for providing automated alarm management in accordance with a first embodiment.

FIG. 4 illustrates a block diagram of a method 400 for providing automated alarm management in accordance with a first embodiment. The method 400 starts with a wearable sensor device (such as the wearable sensor device 100) being attached to a user/patient for measuring/detecting a plurality of vital sign responses/signals, via step 402. The wearable sensor device continuously generates a vital sign variable X and consider a $K^{th}$ sample of X as $X_k$, via step 404, is input to a moving window of m samples, via step 406, that shifts/slides forward by excluding the $1^{st}$ sample of the window and including the latest sample (e.g., K) in the window as $m^{th}$ sample. In one embodiment, the moving window of m samples is a real positive array denoted $V^m = \{X_{k-m+1}, X_{k-m+2}, \ldots, X_k\}$ where the number of samples m includes but is not limited to 10, 20, and 30 samples and X is a vital sign for example, HR. The moving window $V^m$ of m samples correspond to a desired time duration. Depending on the sampling rate of the vital sign signal and the desired time duration, the number of samples m can be calculated as desired time duration x sampling rate. Accordingly, in one embodiment, if the time duration includes but not limited to 20, 40, 60 seconds and the sampling rate is 0.5 Hz, then the samples of the moving window m can be 10, 20, 30, respectively.

In the method 400, T is the threshold of the vital sign signal/value and the threshold varies based upon the particular vital sign signal/value being monitored (e.g., different thresholds for HR versus BR). In one embodiment, the HR magnitude thresholds are 100, 110, 129, and 139 and the BR magnitude thresholds are 24, 32, and 42. In the method 400, A is the alarm signal (A={0,1}) to be generated for a corresponding sample number k of the vital sign signal/value, where A's value 1 indicates the alarm ON and A's value 0 indicates the alarm OFF.

Referring back to FIG. 4, after providing the moving window via step 406, the method 400 determines whether all of the m samples of $V^m$ greater than or equal to the threshold T, via step 408. If yes (all m samples of $V^m$ are greater than or equal to the predetermined threshold T), then the alarm is set to on ($A_k=1$) and is sounded alerting the user/clinician/third party, via step 410. If no (not all m samples of $V^m$ are greater than or equal to the predetermined threshold T), then the alarm is set to off ($A_k=0$) and is not sounded (i.e., the wearable sensor device doesn't sound an alarm so remains silent or sends an 'OK' alert), via step 412. After sounding the alarm via step 410 or determining that no alarm should be sounded via step 412, the sample number is increased (e.g., k=k+1), via step 414, and the method 400 is repeated by the wearable sensor device for the new sample ($X_k$).

Figure 5:
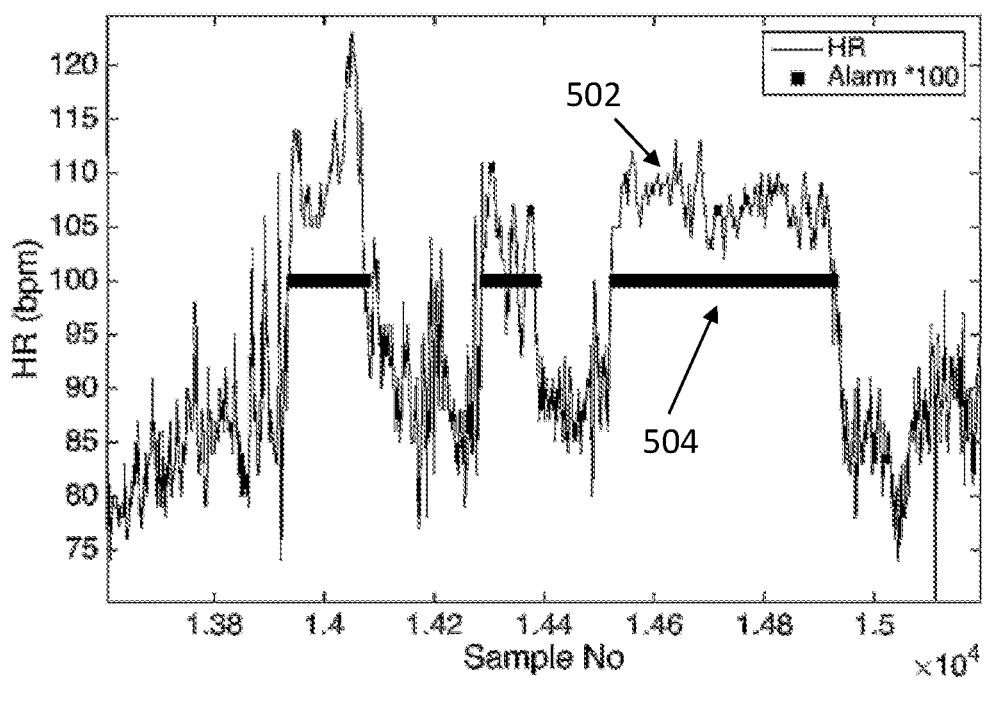
FIG. 5 illustrates a diagram of automated alarm management for heart rate (HR) signals using a wearable sensor device in accordance with an embodiment.

FIG. 5 illustrates a diagram 500 of automated alarm management for heart rate (HR) signals using a wearable sensor device in accordance with an embodiment. The diagram 500 includes the HR in beats per minute (bpm) on the y-axis and the sample number on the x-axis. The plot shows the HR series or signals 502 (black line) along with a plurality of alarms (rectangle blocks) that are generated and scaled as (A×T) for comparison with the HR series 502 where the threshold T was predetermined as 100 bpm. In FIG. 5, an alarm 504 of the plurality of alarms is generated approximately between sample numbers 14500 and 14900, when the detected HR is elevated above the threshold T of 100. The method 400 describes automated generation of alarms when the HR has increased above the 100 bpm threshold and lasts for at least 20 seconds. The onset and offset of alarm are shown as a "square" shape marker with value 100 and 0 respectively in FIG. 5 and the offset value of zero is not shown due to scaling of y-axis.

Figure 6:
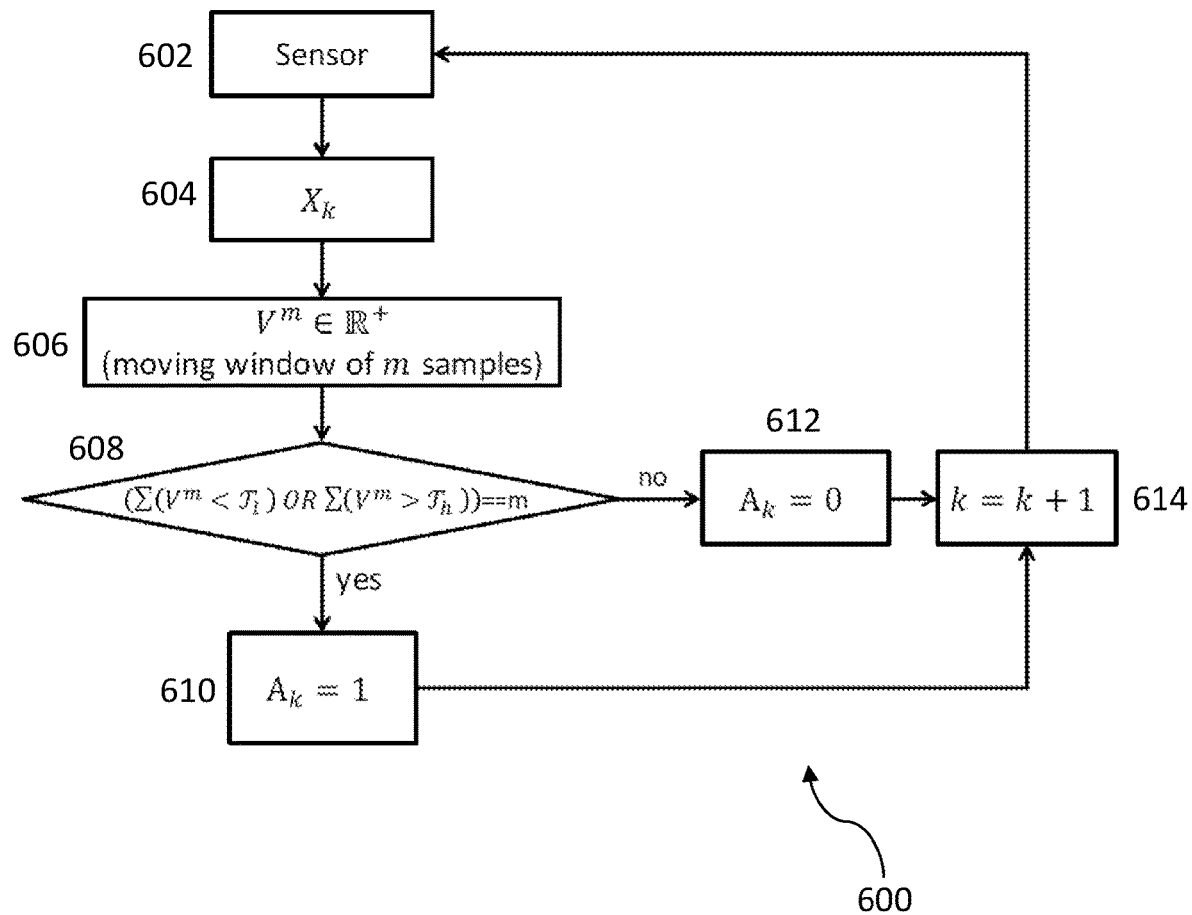
FIG. 6 illustrates a block diagram of a method for providing automated alarm management in accordance with a second embodiment.

FIG. 6 illustrates a block diagram of a method 600 for providing automated alarm management in accordance with a second embodiment. In the method 400 of FIG. 4, the magnitude threshold only has an upper limit including but not limited to 100 bpm which enables alarming for elevation in vital sign/value above the upper limit, which is the most likely scenario in clinical monitoring. However, there are instances of unexpected decreases in vital sign values below a lower limit including but not limited to 30 bpm, which also needs to be alerted. Therefore, the method 600 addresses such a need to consider upper and lower magnitude threshold limits to trigger the alarms while monitoring with a wearable sensor device.

The method 600 starts with a wearable sensor device (such as the wearable sensor device 100) being attached to a user/patient for measuring/detecting a plurality of vital sign responses/signals, via step 602. The wearable sensor device continuously generates a vital sign signal X and consider a $K^{th}$ sample of X as $X_k$, via step 604, is input to a moving window of m samples, via step 406, that shifts/slides forward by excluding the $1^{st}$ sample of the window and including the latest sample (e.g., K) in the window as $m^{th}$ sample. In one embodiment, the moving window of m samples is a real positive array denoted $V^m = \{X_{k-m+1}, X_{k-m+2}, \ldots, X_k\}$ where the number of samples m includes but is not limited to 10, 20, and 30 samples and X is a vital sign (e.g., HR). The moving window $V^m$ of m samples correspond to a desired time duration.

In one embodiment of the method 600 of FIG. 6, similar to method 400 of FIG. 4, if the time duration includes but not limited to 20, 40, 60 seconds and the sampling rate is 0.5 Hz, then the samples of the moving window m can be 10, 20, 30, respectively. In the method 600, $T_l$ is the lower bound threshold of the vital sign signal/value and $T_h$ is the upper bound threshold of the vital sign signal/value. Each threshold (lower and upper) varies based upon the particular vital sign signal/value being monitored (e.g., there are different predetermined thresholds for HR versus BR). In one embodiment, the HR magnitude thresholds are 40 for $T_l$ and 100 for $T_h$ and the BR magnitude thresholds are 6 for $T_l$ and 24 for $T_h$. In the method 600, A is the alarm signal (A={0,1}; 1 is ON and 0 is OFF) to be generated for a corresponding sample number k of the vital sign signal/value.

Referring back to FIG. 6, after providing the moving window via step 606, the method 600 determines whether all of the m samples of $V^m$ are outside (either below or above) the lower and upper bound thresholds $T_l$ and $T_h$ per the following equation: $(\Sigma(V^m < T_l) \text{ OR } \Sigma(V^m > T_h)) = m$, via step 608. If yes and the condition is satisfied (all m samples of $V^m$ are either less than the lower threshold $T_l$ or greater than the upper threshold $T_h$), then the alarm is set to on ($A_k$=1) and is sounded alerting the user/clinician/third party, via step 610. In another embodiment, the condition to be satisfied can be ($\Sigma(V^m \leq T_l)$ OR $\Sigma(V^m \geq T_h)$)==m.

If no and the condition is not satisfied (not all m samples of $V^m$ are either less than the lower threshold $T$ or greater than the upper threshold $T_h$), then the alarm is set to off ($A_k$=0) and is not sounded (i.e., the wearable sensor device doesn't sound an alarm so remains silent or sends an 'OK' alert), via step 612. After sounding the alarm via step 610 or determining that no alarm should be sounded via step 612, the sample number is increased (e.g., k=k+1) and the method 600 is repeated by the wearable sensor device for the new sample ($X_k$), via step 614.

In addition to setting fixed predetermined thresholds for the automated alarm management, the method and system in accordance with the present invention also utilizes variable, dynamic, and customized thresholds in another embodiment. The customization of the thresholds can be utilized when a user/patient has a higher basal heart rate level and so predetermined thresholds might not be as accurate when determining abnormal levels thereby sounding off the alarms.

For example, individuals with high basal heart rate (HR) values close to traditional thresholds like 100 bpm may tend to generate many false positive alarms (i.e., an alarm is generated indicating a potential issue when there actually is nothing wrong and an alarm should not have been triggered). In addition, individuals with low basal HR values may not surpass the traditional thresholds like 140 bpm despite significant and drastic changes in the HR while in rest which may tend to generate many false negative alarms (i.e., no alarm is sounded when there is something potentially wrong and an alarm should have been sounded).

Furthermore, the basal values in individuals can vary drastically in 24 hour time periods (or other predetermined time periods) and so traditional thresholds (whether lower or upper bounds) are not as effective in generating the necessary alarms over the 24 hour time period associated with continuous monitoring settings (in the hospital or at home) using wearable sensor devices. Therefore, the method and system in accordance with the present invention provides an automated alarm management that adaptively varies the alarm thresholds that are customized for the given individual (i.e., the thresholds for one user will be different than the thresholds for another user) to provide more accurate alerts regarding unusual changes to critical vital sign signals.

In one embodiment, the adaptive/dynamic thresholds are determined based upon the user's detected vital signs over a predetermined time period and are independent of traditional predetermined/fixed thresholds. In another embodiment, the thresholds are determined using a combination of predetermined thresholds, the customized thresholds based on the user's historical data, and the thresholds of a plurality of users that are stored and aggregated in a database and analyzing to learn the most appropriate thresholds in varying conditions that are based on metrics including but not limited to the user's demographics, current activities, and medical history.

Figure 7:
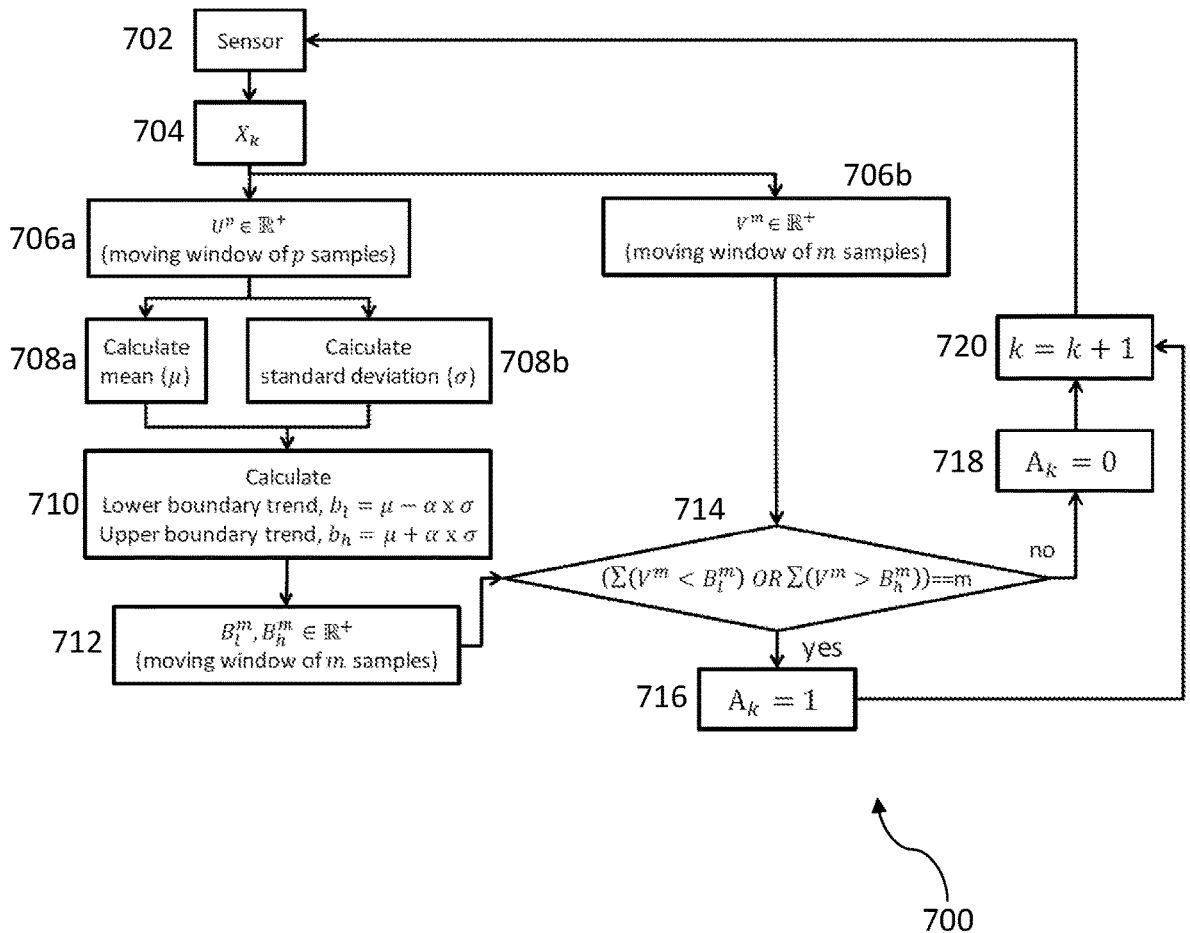
FIG. 7 illustrates a block diagram of a method for providing adaptive alarm management in accordance with an embodiment.

FIG. 7 illustrates a block diagram of a method 700 for providing adaptive alarm management in accordance with an embodiment. The method 700 is similar to the method 200 of FIG. 2 and the method 600 of FIG. 6 with the additional components of an adaptive threshold determination by the wearable sensor device. The adaptive alarm management provided by the method 700 is also automated. The method 700 starts with a wearable sensor device (such as the wearable sensor device 100) being attached to a user/patient for measuring/detecting a plurality of vital sign responses/signals, via step 702. The wearable sensor device continuously generates a a vital sign signal X and considering $K^{th}$ sample of X as $X_k$, via step 704.

In FIG. 7, the $K^{th}$ sample of X is input to two simultaneous moving windows, via step 706a and 706b. The first moving window $U^p$ provided by step 706a and is a moving window of p samples wherein the moving window is a real positive array where $U^p = \{X_{k-p+1}, X_{k-p+2}, \ldots, X_k\}$. The second moving window $V^m$ is provided by step 706b and is a sample moving window of m samples wherein the moving window is a real positive array where $V^m = \{X_{k-m+1}, X_{k-m+2}, \ldots, X_k\}$. In one embodiment, step 706b is carried out simultaneously with step 706a and in another embodiment, step 706b is carried out after the trend boundary is calculated.

The first moving window array $U^p$ as in step 706a is relatively larger to help track the trend changes in vital sign signal/value and allows the generation of adaptive statistical based thresholds for generating alarms. On the other hand, the second moving window array $V^m$ as in step 706b enables checking whether the m samples of vital sign signal satisfy the adaptive upper and lower magnitude thresholds and time duration to trigger the alarms, via step 714.

In FIG. 7, using the p samples of the vital sign signal stored in the first moving window via step 706a, the method 700 calculates a mean ($\mu$), via step 708a, and a standard deviation ($\sigma$), via step 708b. After calculating both the mean and standard deviation via steps 708a-b, the method 700 calculates a lower boundary trend ($b_l$) and an upper boundary trend ($b_h$) which represent the lower and upper statistical boundaries respectively (also referred to as a trend boundary), via step 710 as adaptive magnitude thresholds for generating alarms. The lower boundary trend of the trend boundary is calculated as $b_l = \mu - \alpha^* \sigma$ (similar to the lower limit calculated in the method 200 of FIG. 2) and the upper boundary trend of the trend boundary is calculated as $b_h = \mu + \alpha^* \sigma$ where alpha ($\alpha$) is a factor or coefficient including but not limited 1, 1.1, 1.2 . . . , 2.0, etc.

Once the lower and upper boundary trend values $b_l$ and $b_h$, respectively, are determined via step 710, the method 700 tracks the calculated $b_l$ and $b_h$ values separately in dual moving window arrays $B_l^m$ and $B_h^m$, respectively, via step 712, where $B^m$ is a real positive array, $B^m = \{b_{k-m+1}, b_{k-m+2}, \ldots, b_k\}$, with m as number of samples as in step 706b. The dual moving window arrays $B_l^m$ and $B_h^m$ are calculated using a dual moving window and represent two separate real positive arrays (dual real positive array). The method 700 utilizes the dual real positive array that comprises the lower and upper boundary arrays ($B_l^m$ and $B_h^m$) from step 712 and the vital sign signal array $V^m$ from step 706b to check whether all of the m samples of $V^m$ are outside the lower and upper statistical boundary arrays ($B_l^m$ and $B_h^m$ respectively, also referred to as an adaptive trend boundary) that are outputted from step 712 per the following equation: ($\Sigma(V^m < B_l^m)$ OR $\Sigma(V^m > B_h^m)$)==m, via step 714.

If yes (all m samples of $V^m$ are either less than the lower threshold $B_l^m$ or greater than the upper threshold $B_h^m$ and are therefore outside of the adaptive trend boundary), then the alarm is set to on ($A_k$=1) and is sounded alerting the user/clinician/third party, via step 716. If no (not all m samples of $V^m$ are either less than the lower threshold $B_l^m$ or greater than the upper threshold $B_h^m$), then the alarm is set to off ($A_k$=0) and is not sounded (i.e., the wearable sensor device doesn't sound an alarm so remains silent or sends an 'OK' alert), via step 718. After sounding the alarm via step 716 or determining that no alarm should be sounded via step 718, the sample number is increased (e.g., k=k+1) and the method 700 is repeated by the wearable sensor device for the new sample ($X_k$), via step 720. In addition, once the m samples of $V^m$ are determined to be within the adaptive trend boundary, the alarm that was previously sounded is then turned off automatically.

In one embodiment, only when all of the m samples satisfy the condition of step 714, will the elevation in the response fulfill the desired duration of elevation as m is proportional to the duration. If not all of the m samples are either lower or higher (and thus outside the boundaries), the alarm will not be triggered. If the elevation is sustained and true, the alarm will be delayed until all m samples satisfy the condition of step 714 (which thereby affirms the true positive occurrence of the alarm). If the elevation is not sustained (all the m samples do not satisfy the condition of step 714), then the elevation can be a false positive due to artifacts/motion/noise as aforementioned in the method 200 and thus an alarm would not be sounded.

In the method 700, instead of fixed thresholds as $T_l$ and $T_h$ in method 600, the lower and upper thresholds for alarming in method 700 are adaptively determined as $b_l$ and $b_h$, respectively, and are tracked in arrays of $B_l^m$ and $B_h^m$ for sample-to-sample comparison with $V^m$. In one embodiment of the method 700 of FIG. 7, the parameters include but are not limited to 50, 100, 150, etc. for p, 10, 20, 30, etc. for m, and 1.0, 1.1, 1.2, etc. for alpha (a). In the method 700, A is the alarm signal (A={0,1}; 0 is OFF and 1 is ON) to be generated for a corresponding sample number k of the vital sign signal/value.

Figure 8:
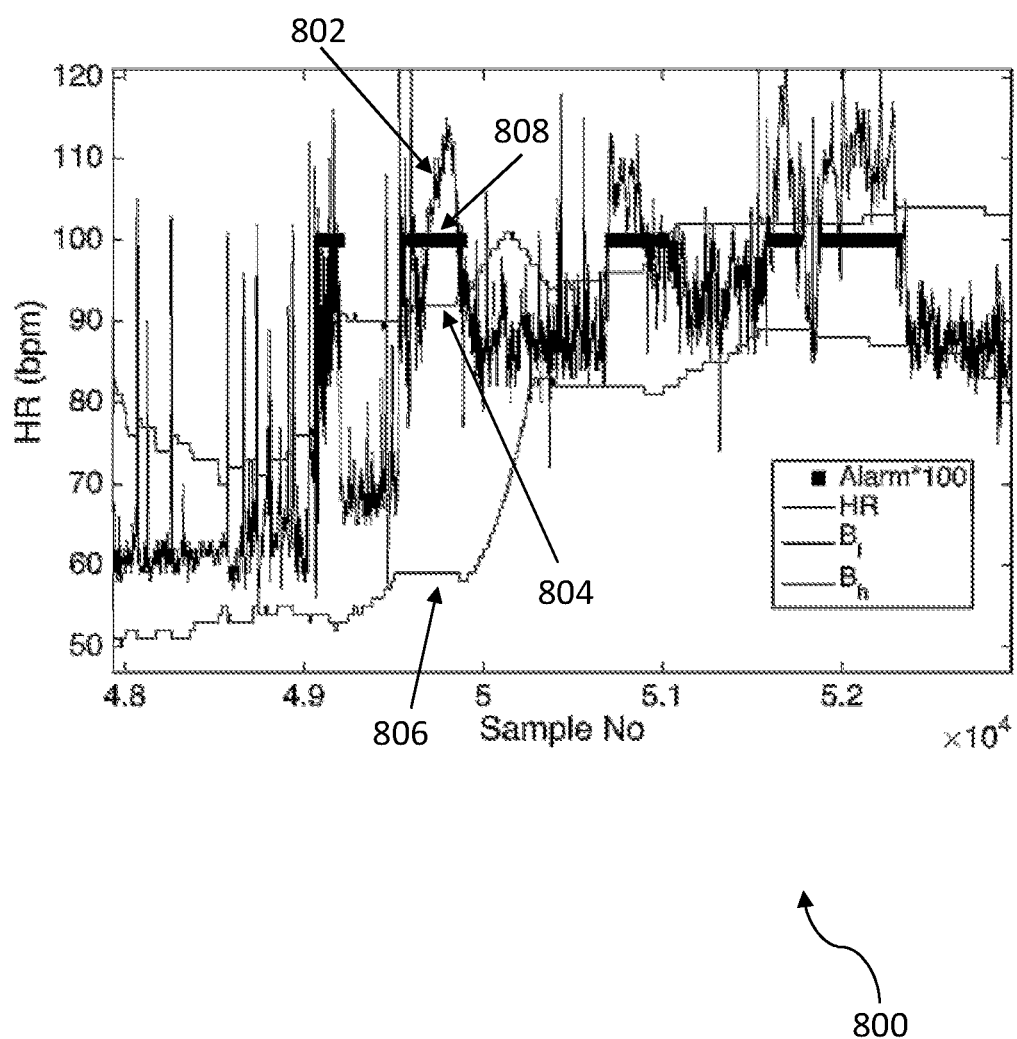
FIG. 8 illustrates a diagram of adaptive alarm management for heart rate (HR) signals using a wearable sensor device in accordance with an embodiment.
Figure 9:
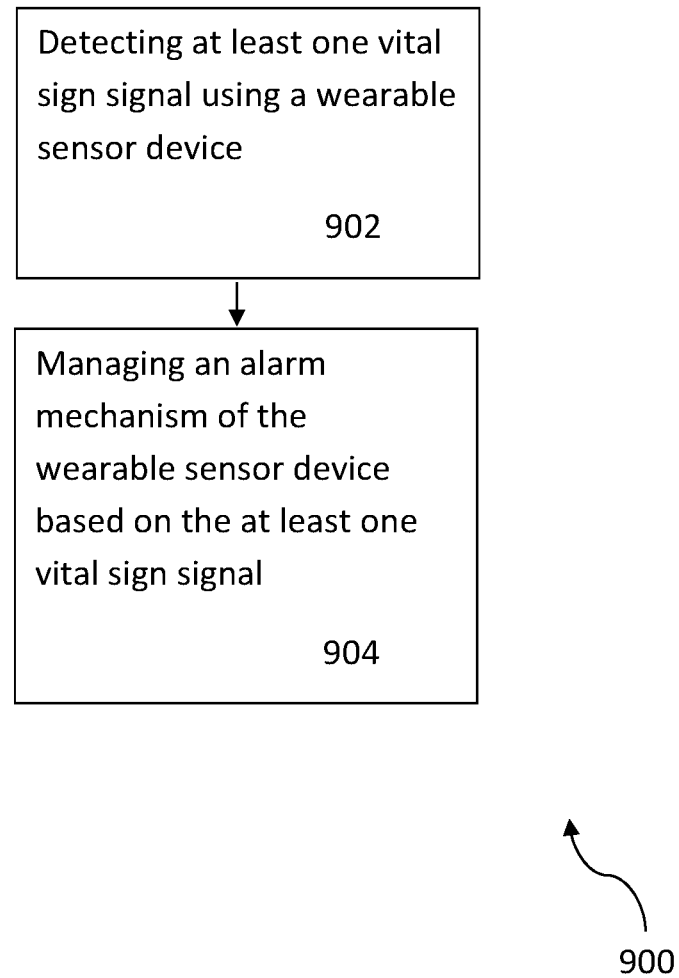
FIG. 9 illustrates a method for providing health-monitoring alarm management in accordance with an embodiment.

FIG. 8 illustrates a diagram 800 of adaptive alarm management for heart rate (HR) signals using a wearable sensor device in accordance with an embodiment. The diagram 800 includes the HR in beats per minute (bpm) on the y-axis and the sample number on the x-axis. The plot shows the HR series (or signals) 802 (black line), an upper threshold boundary $B_h$ 804, a lower threshold boundary $B_l$ 806, and a plurality of alarms (rectangle blocks) that are generated and scaled as (A×100) in FIG. 8 for comparison with the HR series 802. However, the generated alarm signal A is 1 when the alarm is ON.

In FIG. 8, the upper and lower thresholds 804 and 806 are dynamically and adaptively determined using the user's vital sign/signal values in accordance with the method 700 of FIG. 7. In another embodiment, an aggregation of data from a plurality of users is utilized to adaptively determine the upper and lower thresholds. In FIG. 8, one alarm 808 of the plurality of alarms is generated between sample number 49500 and 50000 since the vital sign/signal values 802 are outside the threshold limits of 804 and 806. Thus, alarms are automatically turned ON when the vital sign/signal values are outside the upper and lower threshold boundaries. When the vital sign/signal values become within the upper and lower threshold boundaries, the alarms are automatically turned OFF as in FIG. 8.

In one embodiment, in accordance with the present invention, the wearable sensor system with vital sign artifact/outlier removal (of method 200 of FIG. 2), wearable sensor system with automated alarm management using fixed thresholds (of methods 400 and 600 of FIGS. 4 and 6) and the adaptive and automated management system (of method 700) are used on their own to effectively control health-monitoring alarms. In another embodiment, the method and system in accordance with the present invention combines the artifact filtration system (of method 200 of FIG. 2) with either the automated management system (of methods 400 and 600 of FIGS. 4 and 6) or the adaptive and automated management system (of method 700 of FIG. 7) to effectively control health-monitoring alarms based upon varying situation.

A method for providing health-monitoring alarm management is provided. In one embodiment, the method comprises detecting at least one vital sign signal using a wearable sensor device and managing an alarm mechanism of the wearable sensor device based on the at least one vital sign signal. The method utilizes a plurality of moving windows that provide a plurality of real positive arrays (arrays that comprise positive numbers) thereby enabling the automation and control of the alarms. In another embodiment, the outputted arrays comprise either negative numbers or imaginary numbers.

In a first embodiment, the managing of the alarm mechanism of the wearable sensor device further comprises statistical based filtering of the at least one vital sign signal, wherein a moving window of a predetermined number of samples applied to a current sample provides a real positive array. In the first embodiment, the managing further comprises determining a mean value and a standard deviation value using the real positive array.

In the first embodiment, the method includes determining a statistical boundary comprising a lower threshold and an upper threshold, wherein the lower threshold and the upper threshold are calculated using the mean value, the standard deviation value, and a coefficient parameter. The method includes determining whether the current sample is within the statistical boundary and in response to the current sample being outside the statistical boundary, labeling the current sample as an artifact and replacing the current sample with the mean value. This system reduces the false positive alarms generated by artifact spikes in vital sign signals.

In a second embodiment, the managing of the alarm mechanism of the wearable sensor device further comprises applying a moving window of a predetermined number of samples to a current sample of the at least one vital sign signal to provide a real positive array, determining whether the predetermined number of samples of the real positive array are greater than or equal to a predetermined upper threshold, and in response to the predetermined number of samples being greater than or equal to the predetermined upper threshold, sounding an alarm.

In a third embodiment, the managing of the alarm mechanism of the wearable sensor device further comprises applying a moving window of a predetermined number of samples to a current sample of the at least one vital sign signal to provide a real positive array, determining whether the predetermined number of samples of the real positive array are within a predetermined boundary comprising a lower threshold and an upper threshold, and in response to the predetermined number of samples being outside the predetermined boundary, sounding an alarm. In the third embodiment, the lower threshold and the upper threshold of the predetermined boundary are selected based upon a type of the at least one vital sign signal.

In a fourth embodiment, the automated alarm management system includes determining continuous adaptive statistical threshold trends (or an adaptive trend boundary) comprising a lower threshold value trend and an upper threshold value trend instead of a preset single lower threshold value and a preset upper threshold value as in the third embodiment. The lower and upper adaptive statistical threshold trends are calculated using a coefficient (preselected) and mean and standard deviation values that are calculated from a first moving window of a predetermined number of samples applied to a current sample of the at least one vital sign signal.

In the fourth embodiment, the samples of the vital sign signal and the lower and upper adaptive statistical threshold values are passed through moving windows of a different predetermined number of samples. The method determines if all the moving window samples of vital sign signal are within the adaptive trend boundary, and in response to the predetermined number of vital sign samples being outside the adaptive trend boundary, sounding an alarm, wherein once the predetermined number of samples are no longer outside the adaptive trend boundary, turning off the alarm.

In the fourth embodiment, the managing of the alarm mechanism of the wearable sensor device further comprises applying a first moving window of a predetermined number of samples to a current sample of the at least one vital sign signal to provide a first real positive array and determining a mean value and a standard deviation value using the first real positive array.

In the fourth embodiment, the method includes determining a trend boundary comprising a lower threshold and an upper threshold, wherein the lower threshold and the upper threshold are calculated using the mean value, the standard deviation value, and a coefficient parameter. The method includes determining a dual moving window of a predetermined number of samples based on the trend boundary to provide a dual real positive array. The dual real positive array is defined as a second real positive array correlative to the lower boundary of the trend boundary and as a third real positive array correlative to the upper boundary of the trend boundary.

The method includes applying a fourth moving window of a predetermined number of samples to the current sample of the at least one vital sign signal to provide a fourth real positive array, combining the dual real positive array and the fourth real positive array to provide the adaptive trend boundary, determining whether the predetermined number of samples of the second real positive array are within the adaptive trend boundary, and in response to the predetermined number of samples being outside the adaptive trend boundary, sounding an alarm, wherein once the predetermined number of samples are no longer outside the adaptive trend boundary, turning off the alarm.

A system for providing health-monitoring alarm management is provided. In one embodiment, the system comprises a sensor for detecting at least one vital sign signal, a processor coupled to the sensor, and a memory device coupled to the processor, wherein the memory device stores an application which, when executed by the processor, causes the processor to manage an alarm mechanism of the wearable sensor device based on the at least one vital sign signal. The system carries out the steps of at least the first, the second, the third, and the fourth embodiments of the aforementioned method.

As above described, a method and system in accordance with the present invention provides a wearable sensor device that more effectively manages monitoring alarms by filtering artifacts/noise/spikes from the detected vital signs and by providing both an automated alarm management using preset alarm thresholds and adaptive automated alarm management using customized adaptively determined alarm thresholds. The method and system enable adaptive and continuous varying of the alarm thresholds that are customized to the individual user that allow automatic turning on and off of the alarms during the clinical monitoring of the user.

The artifacts/spikes of the vital sign signals (e.g., heart rate HR) are filtered out using a statistical filtering methodology to reduce false positive alarms. The alarms and their frequency are controlled and automatically generated using features of the vital sign signals and predetermined thresholds. In addition, the thresholds are adaptively varied and adjusted to provide further precision of the management of the alarms that are customized based upon the user/individual being monitored.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for providing health-monitoring alarm management, the method comprising:

detecting at least one vital sign signal of a patient using a wearable sensor device, wherein the wearable sensor device monitors a plurality of vital sign signals continuously; and managing an alarm mechanism of the wearable sensor device, wherein the managing the alarm mechanism comprises:

removing artifacts using statistical filtering, wherein statistical filtering includes:

using a moving window of a predetermined number of samples of the at least one vital sign signal to determine a statistical boundary comprising a lower limit (LL) and an upper limit (UL) and comparing a current sample to the statistical boundary, wherein if the current sample is determined to be within the statistical boundary, the current sample value is not modified and the sample number is incremented, and if the current sample is not determined to be within the statistical boundary, the current sample value is determined to be an outlier and is replaced with the previously determined mean value and the sample number is incremented; and adaptively varying vital sign alarm thresholds using magnitude and duration of vital sign signals with respect to pre-determined thresholds to provide dynamically customized alarm thresholds for the patient.

2. The method of claim 1, wherein the managing further comprises:

filtering the at least one vital sign signal using a statistical filtration mechanism, wherein the statistical filtration mechanism applies a moving window of a predetermined number of samples to a current sample of the at least one vital sign signal to provide a real positive array; and determining a mean value and a standard deviation value using the real positive array.

3. The method of claim 2, wherein the lower threshold and the upper threshold are calculated using the mean value, the standard deviation value, and a coefficient parameter.

4. The method of claim 3, further comprising:
   determining whether the current sample is within the statistical boundary; and
   in response to the current sample being outside the statistical boundary, labeling the current sample as an artifact and replacing the current sample with the mean value.

5. The method of claim 1, wherein the managing further comprises:
   applying the moving window of the predetermined number of samples to the current sample of the at least one vital sign signal to provide a real positive array;
   determining whether the predetermined number of samples of the real positive array are greater than or equal to a predetermined upper threshold; and
   in response to the predetermined number of samples being greater than or equal to the predetermined upper threshold, sounding an alarm.

6. The method of claim 1, wherein the managing further comprises:
   applying a moving window of a predetermined number of samples to a current sample of the at least one vital sign signal to provide a real positive array;
   determining whether the predetermined number of samples of the real positive array are within a predetermined boundary comprising a lower threshold and an upper threshold; and
   in response to the predetermined number of samples being outside the predetermined boundary, sounding an alarm.

7. The method of claim 6, wherein the lower threshold and the upper threshold of the predetermined boundary are selected based upon a type of the at least one vital sign signal.

8. The method of claim 1, wherein the managing further comprises:
   applying a first moving window of a predetermined number of samples to a current sample of the at least one vital sign signal to provide a first real positive array;
   determining a mean value and a standard deviation value using the first real positive array.

9. The method of claim 8, further comprising:
   determining a trend boundary comprising a lower threshold and an upper threshold, wherein the lower threshold and the upper threshold are calculated using the mean value, the standard deviation value, and a coefficient parameter.

10. The method of claim 9, further comprising:
    determining a dual moving window of a predetermined number of samples based on the trend boundary to provide a dual real positive array.

11. The method of claim 10, further comprising:
    applying a fourth moving window of a predetermined number of samples to the current sample of the at least one vital sign signal to provide a fourth real positive array; and
    combining the dual real positive array and the fourth real positive array to provide an adaptive trend boundary;
    determining whether the predetermined number of samples of the fourth real positive array are within the adaptive trend boundary; and
    in response to the predetermined number of samples being outside the adaptive trend boundary, sounding an alarm, wherein once the the predetermined number of samples are no longer outside the adaptive trend boundary, turning off the alarm.

12. A system for providing health-monitoring alarm management, the system comprising a wearable sensor for detecting at least one vital sign signal of a patient, a processor coupled to the sensor, and a memory device coupled to the processor, wherein the memory device stores an application which, when executed by the processor, causes the processor to:
    detect at least one vital sign signal of a patient using the wearable sensor device, wherein the wearable sensor device monitors a plurality of vital sign signals continuously; and
    manage an alarm mechanism of the wearable sensor device, wherein the management of the alarm mechanism comprises:
       removing artifacts using statistical filtering, wherein statistical filtering includes:
          using a moving window of a predetermined number of samples of the at least one vital sign signal to determine a statistical boundary comprising a lower limit (LL) and an upper limit (UL) and comparing a current sample to the statistical boundary, wherein
             if the current sample is determined to be within the statistical boundary, the current sample value is not modified and the sample number is incremented, and
             if the current sample is not determined to be within the statistical boundary, the current sample value is determined to be an outlier and is replaced with the previously determined mean value and the sample number is incremented; and
       adaptively varying vital sign alarm thresholds using magnitude and duration of vital sign signals with respect to pre-determined thresholds to provide dynamically customized alarm thresholds for the patient.

13. The system of claim 12, wherein to manage further comprises to:
    filter the at least one vital sign signal using a statistical filtration mechanism of the application, wherein the statistical filtration mechanism applies a moving window of a predetermined number of samples to a current sample of the at least one vital sign signal to provide a real positive array; and
    determine a mean value and a standard deviation value using the real positive array.

14. The system of claim 13, wherein the lower threshold and the upper threshold are calculated using the mean value, the standard deviation value, and a coefficient parameter.

15. The method of claim 14, wherein the application further causes the processor to:
    determine whether the current sample is within the statistical boundary; and
    in response to the current sample being outside the statistical boundary, label the current sample as an artifact and replace the current sample with the mean value.

16. The system of claim 12, wherein to manage further comprises to:
    apply the moving window of the predetermined number of samples to the current sample of the at least one vital sign signal to provide a real positive array;
    determine whether the predetermined number of samples of the real positive array are greater than or equal to a predetermined upper threshold; and
    in response to the predetermined number of samples being greater than or equal to the predetermined upper threshold, sound an alarm.

17. The system of claim 12, wherein to manage further comprises to:
- apply a moving window of a predetermined number of samples to a current sample of the at least one vital sign signal to provide a real positive array;
- determine whether the predetermined number of samples of the real positive array are within a predetermined boundary comprising a lower threshold and an upper threshold; and
- in response to the predetermined number of samples being outside the predetermined boundary, sound an alarm.

18. The system of claim 12, wherein to manage further comprises to:
- apply a first moving window of a predetermined number of samples to a current sample of the at least one vital sign signal to provide a first real positive array;
- determine a mean value and a standard deviation value using the first real positive array.

19. The system of claim 18, wherein the application further causes the processor to:
- determine a trend boundary comprising a lower threshold and an upper threshold, wherein the lower threshold and the upper threshold are calculated using the mean value, the standard deviation value, and a coefficient parameter; and
- determine a dual moving window of a predetermined number of samples based on the trend boundary to provide a dual real positive array.

20. The system of claim 19, wherein the application further causes the processor to:
- applying a fourth moving window of a predetermined number of samples to the current sample of the at least one vital sign signal to provide a fourth real positive array; and
- combine the dual real positive array and the fourth real positive array to provide an adaptive trend boundary;
- determine whether the predetermined number of samples of the dual real positive array are within the adaptive trend boundary; and
- in response to the predetermined number of samples being outside the adaptive trend boundary, sounding an alarm, wherein once the the predetermined number of samples are no longer outside the adaptive trend boundary, turning off the alarm.

\* \* \* \* \*